(12) United States Patent
Becker et al.

(10) Patent No.: US 8,735,813 B2
(45) Date of Patent: May 27, 2014

(54) METHOD AND DEVICE FOR CARRYING OUT A QUANTITATIVE SPATIALLY RESOLVED LOCAL ANALYSIS AND DISTRIBUTION ANALYSIS OF CHEMICAL ELEMENTS AND IN SITU CHARACTERIZATION OF ABLATED SURFACE REGIONS

(71) Applicant: Forschungszentrum Juelich GmbH, Juelich (DE)

(72) Inventors: Sabine Becker, Vettweiss (DE); Dagmar Salber, Lontzen (BE)

(73) Assignee: Forschungszentrum Juelich GmbH, Juelich (DE)

( * ) Notice: Subject to any disclaimer, the term of this patent is extended or adjusted under 35 U.S.C. 154(b) by 0 days.

(21) Appl. No.: 13/849,915

(22) Filed: Mar. 25, 2013

(65) Prior Publication Data
US 2013/0234015 A1 Sep. 12, 2013

Related U.S. Application Data

(62) Division of application No. 13/138,689, filed on Dec. 9, 2011, now Pat. No. 8,497,470.

(30) Foreign Application Priority Data

Apr. 8, 2009 (DE) .......................... 10 2009 016 512

(51) Int. Cl.
| | |
|---|---|
| H01J 49/04 | (2006.01) |
| H01J 49/26 | (2006.01) |
| G01N 1/00 | (2006.01) |
| B01D 59/44 | (2006.01) |

(52) U.S. Cl.
USPC ............. 250/288; 250/281; 250/282; 356/36; 359/391

(58) Field of Classification Search
USPC .............. 250/281, 288, 282; 356/36; 359/391
See application file for complete search history.

(56) References Cited

U.S. PATENT DOCUMENTS

| | | | |
|---|---|---|---|
| 3,941,567 A | 3/1976 | Combaz | |
| 7,651,856 B2 | 1/2010 | Schuetze et al. | |
| 8,274,735 B2* | 9/2012 | Fry et al. | 359/393 |
| 8,497,470 B2* | 7/2013 | Becker et al. | 250/282 |

(Continued)

FOREIGN PATENT DOCUMENTS

| | | |
|---|---|---|
| DE | 102 34 755 | 2/2004 |
| DE | 103 46 458 | 5/2005 |

(Continued)

OTHER PUBLICATIONS

Hutchinson et al: "Imaging and spatial distributuion of beta-amyloid peptide and metal ions in Alzheimer's plaques by laser ablation-inductively coupled plasma-mass spectrometry" Analytical Biochemistry, Academic Pres SIN, New York LNKD-DOI: 10.1016/J.AB.2005.08.024, vol. 346, No. 2, Nov. 15, 2005, pp. 225-233, XP005126668 ISSN: 003-2697 *abstract; figure 6 p. 226, col. 1, paragraph 2 p. 226, col. 2, paragraph 3 p. 227, col. 1, paragraph 4 p. 230, col. 1, line 1—p. 232, col. 1, last paragraph.

*Primary Examiner* — Nikita Wells
(74) *Attorney, Agent, or Firm* — Jordan and Hamburg LLP

(57) ABSTRACT

A laser ablation chamber, which is suitable for use in a conventional laser-assisted micro dissection unit (LMD), in combination with the LMD allows for both quantitative spatially resolved nanolocal analysis and distribution analysis of element concentrations of a sample, and a microscopic detection of the surface topography of the same sample, in the nanometer range. Optionally, further examinations may follow, without having to remove the sample from a microscope slide bearing the sample. For the examination, a region of the sample to be analyzed is selected with the aid of a microscope of a LMD. For this purpose, the sample is located on the lower face of a cover slip (microscope slide), which also forms part of a laser ablation chamber mounted beneath the microscope slide and inside the LMD. A portion of the sample is ablated and analyzed. Optionally, the existing LMD instrumentation may be used to deliberately cut out certain regions of the tissue in which metals were detected for further analytics and to collect these regions in sample containers, which are mounted beneath the microscope slide after the laser ablation.

8 Claims, 2 Drawing Sheets

(56) References Cited

U.S. PATENT DOCUMENTS

| | | |
|---|---|---|
| 2003/0075530 A1 | 4/2003 | Ganser et al. |
| 2004/0045497 A1 | 3/2004 | Kriews et al. |
| 2006/0121298 A1 | 6/2006 | Wittke et al. |
| 2007/0031816 A1 | 2/2007 | Schuetze et al. |
| 2007/0114394 A1 | 5/2007 | Combs et al. |
| 2008/0247038 A1 | 10/2008 | Sasaki et al. |

FOREIGN PATENT DOCUMENTS

| | | |
|---|---|---|
| DE | 103 54 787 | 6/2005 |
| DE | 103 58 566 | 7/2005 |
| DE | 10 2006 049 638 | 6/2007 |
| JP | 9-133617 | 5/1997 |
| JP | 11-148887 | 6/1999 |
| JP | 199 34 561 | 2/2001 |
| JP | 02/054057 | 7/2002 |
| JP | 2006/076817 | 7/2006 |
| JP | 2007-298392 | 11/2007 |
| WO | WO-01/79911 | 10/2001 |
| WO | WO-2005/033669 | 4/2005 |
| WO | WO-2005/057178 | 6/2005 |
| WO | WO-2007/071985 | 6/2007 |

* cited by examiner

METHOD AND DEVICE FOR CARRYING OUT A QUANTITATIVE SPATIALLY RESOLVED LOCAL ANALYSIS AND DISTRIBUTION ANALYSIS OF CHEMICAL ELEMENTS AND IN SITU CHARACTERIZATION OF ABLATED SURFACE REGIONS

This is a Divisional of U.S. Ser. No. 13/138,689 filed Sep. 19, 2011.

BACKGROUND OF THE INVENTION

The invention relates to a method for local analysis and distribution analysis ("imaging" or "mapping") for the quantitative determination of element concentrations in substrates, in particular in thin tissue sections, of individual cells or cell organelles, and to the in situ characterization of sample surfaces (topography) prior to and after chemical analysis with lateral resolution in the micrometer to nanometer range. The invention further relates to an apparatus that is suitable for carrying out the aforementioned methods.

In element mass spectrometry for direct ablation of the sample material to be examined, various methods, for example using focused laser beams, are employed as analysis methods for the quantitative determination of lateral element distributions with a spatial resolution in the μm range, and for determining trace elements to the ng/g and sub-ng/g concentration range. For example, the method of laser ablation inductively coupled plasma mass spectrometry (LA-ICP-MS) is known, which is employed for trace and isotope analyses, as well as for surface and microlocal analyses on solid sample materials. The disadvantage of this method, however, is that it is not able to determine element distributions and concentrations in thin tissue sections (mapping or imaging analysis) with high lateral resolving power, and notably in the lower microscale and nanoscale range below 5 μm, as is required, for example, for the analysis of individual cells or cell organelles.

In analytics, lasers are increasingly employed, for example the Nd:YAG laser, having a wavelength in the UV range (λ-266 nm or 213 nm). These lasers are frequently used for sample introduction, combined with sensitive ICP mass spectrometers. At present, Nd:YAG laser systems having a laser spot diameter of several μm to several hundred μm are commercially available for microlocal analysis (for example, LSX 213, 500 CETAC Technologies, Ohama, USA, or UP 213, 266 New WAVE Research, Fremont, USA). It is perceived to be a disadvantage that, in general, it is not possible to use such commercial laser ablation systems to directly ablate biological matrices at a lateral resolving power in the lower μm range with high efficiency. The limiting factor here is the diffraction limit below which a laser can generally not go. This means that the minimum possible resolution limit is in the range of the wavelength of the laser. Spatially resolved analyses below 1 μm are therefore generally not possible at all.

Many medical-molecular biological questions, for example regarding the distribution analysis of metals in biological samples (such as in brain sections), however, require that the lateral resolving power of the analysis method used be in the lower micrometer, or several hundred nm range, or as low as the lower nm range. Such spatial resolution could mean that direct nanolocal analytics would be feasible on individual cell organelles. Moreover, many questions demand quantitative information about the metal distribution of diseased tissue sections compared to healthy tissue sections.

Focused IR and UV laser beams are used in commercial instruments (by means of known laser-assisted micro dissection, LMD) to cut out an exactly defined area from a tissue. Laser-assisted micro dissection (LMD), which allows for specific molecular-genetic examination of minimal quantities of a specific tissue, also allows isolated examination of select regions of living individual cells. Such powerful LMD systems having spatial resolution in the lower micrometer range, or at times in the sub-micrometer range, are employed today for isolating and analyzing individual cells or cell areas, for example in the biopsy of individual cancer cells compared to surrounding healthy control cells, or small tissue pieces or DNA strands, for routine research tasks in medicine (pathology), as well as in molecular biology and cell biology. Existing commercial systems offer excellent options for microscopic observation of the sample surfaces and very precise cut-outs of tissue pieces by means of a highly focused laser beam. When using special laser optics, this beam achieves high spatial resolution, as small as the sub-micrometer range (down to 0.5 μm). As differs from laser ablation systems—where the ablation of the sample material is controlled by a defined movement of the specimen stage—the laser beam is moved in a defined manner over the sample surface by means of sophisticated optics having a precision of approximately 0.07 μm. The cut-out tissue samples are subsequently supplied to further offline biomolecular mass spectrometric analysis, typically following tryptic digestion (cell lysis). Quantitative element analysis using LMD online, however, is usually not possible. Compared to commercially available laser ablation systems, such a LMD system has a number of outstanding advantages, such as improved spatial resolution by approximately one order of magnitude, significantly improved microscopic resolution and, in conjunction with special staining techniques (immunostaining) and the use of highly specialized software packages, the detection of special cells (for example, of cancer cells in stained tissue sections).

SUMMARY OF THE INVENTION

It is the object of the invention to provide a simple method that allows qualitative local analysis and distribution analysis in the nanometer range and concurrent quantitative determination of element concentrations in various sample materials, the method also allowing the examined sample surface to be promptly depicted and characterized before and after the analysis, in a simple manner.

It is a further object of the invention to create an apparatus that is suited for carrying out the method.

The objects of the invention are achieved by a method that has all the characteristics of the main claim and by an apparatus that has all the characteristics of the additional independent claim. Advantageous embodiments of the method and of the apparatus are disclosed in the claims relating to them, respectively.

The invention provides a simple method that enables qualitative local analysis and distribution analysis and quantitative determinations of element concentrations in various sample materials in the nanometer range, the method also allowing the topographical sample surface to be examined prior to and after analysis.

It is known that devices for laser-assisted micro dissection (LMD) are already provided with very sophisticated, high resolution optics, which are combined with the ability to cut out previously observed and defined parts of a sample by means of a focused laser beam that is guided in a defined manner over the sample surface. Within the scope of the present invention, it has now been found that the microscope stages having inset microscope slides used to date in the customary laser micro dissection devices can advantageously be modified so that it is now also possible to carry out a laser ablation directly in situ, together with quantitative determination of the element distributions in the selected sample range.

The invention thus combines the advantages of LMD, in terms of the precise cut-out of thin tissue sections of biological samples by defined laser ablation in the examined analysis range with the known line scanning mode, combined with a high resolution microscopic observation of the sample surface, with the benefits of the quantitative element mass spectrometric technique, laser ablation ICP MS. The invention advantageously enables a practical quantification technique for determining the chemical composition of the analyzed samples with respect to metal and non-metal content, as required, for example, in brain research when studying neurodegenerative diseases, the growth of cancerous tissue, aging processes, or questions relating to metal distribution in individual living cells and cell organelles in arbitrary biological sample materials.

In the method according to the invention, the sample that is to be examined, which is located in a laser ablation chamber, is examined microscopically in a first step, and a region for ablation, and thus for the mass spectrometric analysis of the trace elements, is selected. For this purpose, the high resolution optics of a laser-assisted micro dissection device (LMD) can be advantageously employed. In a second step, the laser-induced ablation of the selected region and the distribution analysis of the chemical elements are carried out with the laser that is already present in the LMD. Optionally, this can be done together with at least one selected standard sample, preferably however with a plurality of standard samples, having defined element concentrations for quantifying the chemical elements. Depending on the result, in a third step a corresponding analogous region can then be cut out of the sample for further examination, preferably by laser micro dissection (LMD), and after tryptic digestion of the cut-out tissue, this can be analyzed using biomolecular mass spectrometry with respect to the structural clarification of the metal-binding proteins or phosphoproteins.

One of the advantages of the method according to the invention is that the three aforementioned steps can be carried out by means of a commercial apparatus, in which only a new microscope stage comprising a laser ablation chamber has to be constructed, and the sample, and optionally suitable standards for quantification, can remain permanently on the microscope slide.

This method is made possible by a special laser ablation chamber in which the cover slip, which is transparent to laser light, is formed by a microscope slide that can also be used for laser micro dissection. Both the sample and the standard samples required for analytics (in brain research, typically synthetic lab standards that are adapted to the matrix are employed) can be fixed on this replaceable microscope slide. For the examination, the microscope slide, together with the sample and the standard samples, is introduced into the laser micro dissection device so that the sample and standard samples are located on the lower face of the microscope slide. Before that, the microscope slide is closed with a container forming the lower part of a laser ablation chamber to form an ablation chamber, so that the sample and standard are located at the interior of the chamber. The ablation chamber formed in this way additionally comprises a feed line and a discharge line for transport gas for the ablated material (for example Ar), wherein the discharge line can be connected directly to analytics equipment, notably to an inductively coupled plasma mass spectrometer, ICP-MS. The dimensions of the laser ablation chamber are advantageously selected so that, instead of a regular microscope slide or a microscope slide inserted in a cover slip holder, the entire chamber can be introduced as the microscope stage into an existing laser micro dissection device.

The sample to be examined can first be examined using the existing high resolution optics of the microscope of the LMD apparatus (at approximately 150-fold magnification). For the ablation, the laser, which is likewise present, is focused with an appropriate power density (at a spot diameter of less than 20 µm) on the sample, so that the biological material is completely ablated.

Together with the ablation of the sample material, the standard samples also located on the microscope slide are ablated under the same conditions. The materials of the sample and standards thus ablated are advantageously transported by a carrier gas, for example an argon flow, into the inductively coupled plasma of a highly sensitive and selective ICP mass spectrometer, and ionized. Subsequently, the ions are separated in the separation system of the mass spectrometer in the known manner, and detected. The elemental composition is determined with sensitivity in the ultratrace range, and distribution analysis of the examined sample material is carried out. As an alternative analysis device, ICP-OES may, for example, be considered.

After the results of the distribution analysis of metals and non-metals in the examined sample are available, the method according to the invention can be used to cut out certain analogous regions of the tissue in which metals or phosphorus were detected (for example plaque) for further analytics of the metalloproteins and/or phosphoproteins. For this purpose, the selected regions are ablated (cut out) by means of a focused laser beam and collected in suitable sample containers, which are mounted beneath the microscope slide, after the laser ablation examination.

The laser ablation chamber according to the invention, which is suited to carry out the method, has a modular design. The laser ablation chamber comprises the cover slip, the mount of the cover slip, and the actual flat laser ablation chamber, preferably made of Teflon, to prevent contamination during LA-ICP-MS analysis. The cover slip mount and the remaining laser ablation chamber are connected to each other in a gas-tight manner by way of a means. A suitable means of this sort may be, for example, clamps or screw assemblies, with an additional seal being optionally disposed between the wall of the laser ablation chamber and the cover slip. The cover slip can notably be a typical, conventional microscope slide, which is transparent to the wavelength of the laser light of the LMD device, on the lower face of which the sample and possible standard reference samples can be fixed for examination.

In terms of assembling the laser ablation chamber, for example, first, the cover slip (microscope slide) bearing the sample to be examined and the standard samples on the lower face can be installed in the cover slip mount on a special microscope stage, and subsequently the chamber can be connected in a gas-tight manner to the container, so that no air can flow into the chamber and no Ar transport gas can flow out of the chamber into the surroundings. The ablated material is deliberately transported by the Ar transport gas into the inductively coupled plasma of an ICP-MS.

As an alternative, however, it is also possible for the microscope slide having the sample and a standard sample on the lower face to be first disposed on the container, optionally by means of seals, and to be connected by means of the cover slip mount disposed thereon in a gas-tight manner. Subsequently, the entire laser ablation chamber is introduced in the laser micro dissection device. The LA-ICP-MS chamber developed specifically for the microscope slide is inserted horizontally from the front into the LMD apparatus, prior to element mass spectrometric analysis, using an existing displacement unit.

The entire laser ablation chamber can thus be connected to a laser micro dissection device and advantageously be positioned beneath the lenses by means of the existing positioning units for the object stage of the LMD.

With use of the ablation chamber according to the invention, which is suited for use in a conventional laser-assisted micro dissection device (LMD), microscopic examination can be combined in a simple manner with online LA-ICP-MS examination, and optionally with further examinations, without having to remove the sample from the microscope slide bearing the sample or having to insert the microscope slide in different examination devices.

The subject matter of the invention will be described hereafter in more detail based on two figures, without thereby limiting the subject matter of the invention.

DESCRIPTION OF THE PREFERRED EMBODIMENTS

Figure 1A:
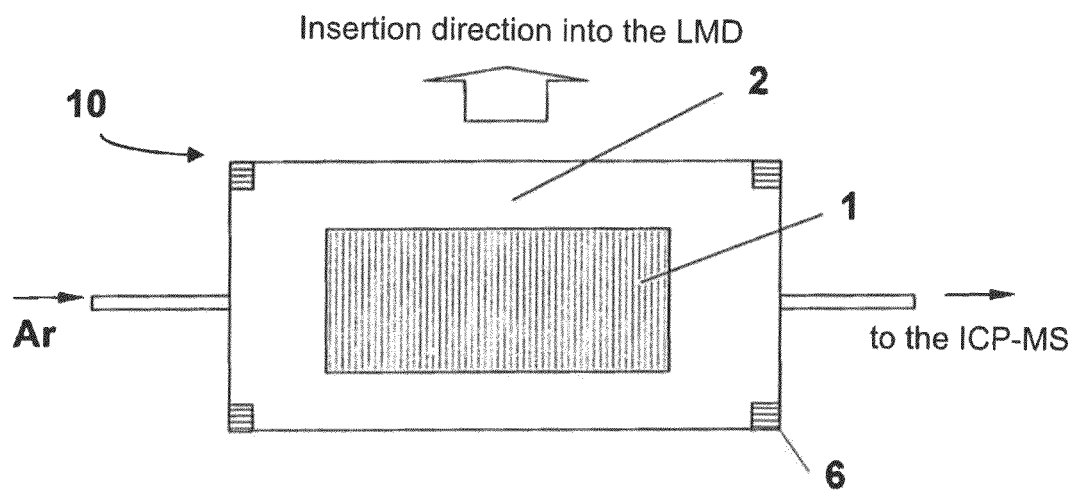
FIGS. 1a and 1b show a detailed arrangement of the laser ablation chamber according to the invention, which can be inserted in a conventional laser micro dissection apparatus (LMD) together with a microscope slide by means of a specially adapted mount, with FIG. 1a being a view of the chamber from above and FIG. 1b being a view of the chamber from the side.
Figure 1B:
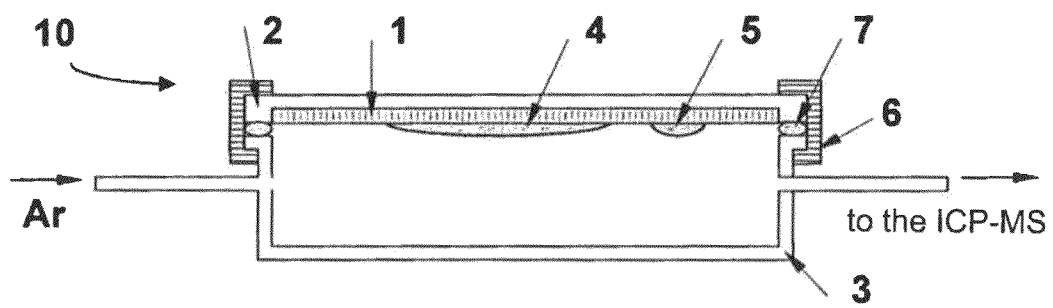
Figure 2:
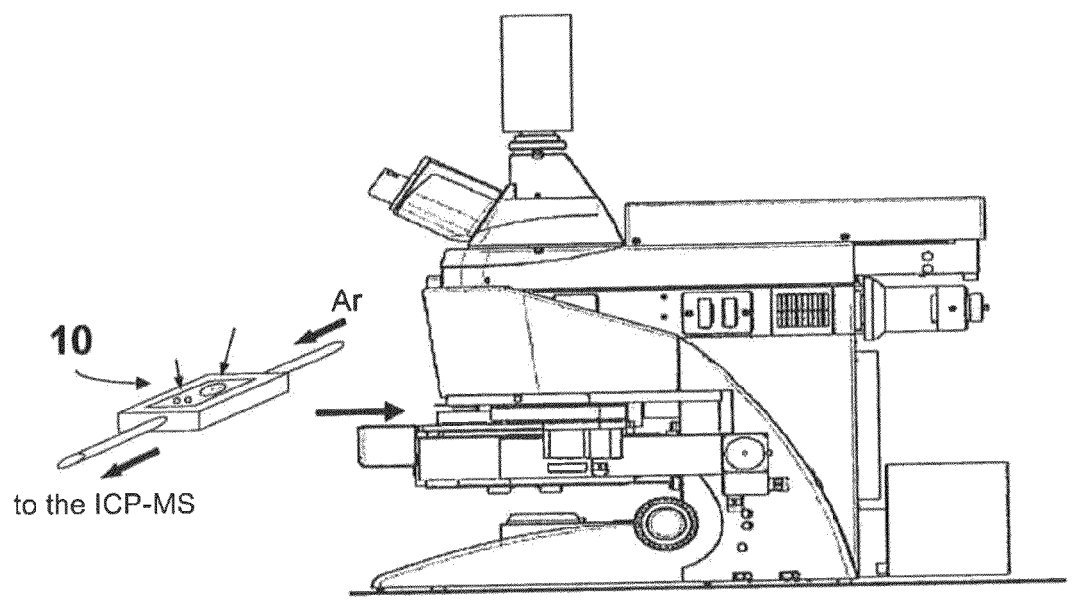
FIG. 2 shows the advantageous combination of the laser ablation chamber according to the invention with the existing laser micro dissection device.

In FIGS. 1 and 2, the following meanings apply:
1 Cover slip, for example a customary microscope slide
2 Cover slip mount
3 Container (lower part of the laser ablation chamber)
4 Sample
5 Standard samples for quantifying the analysis results
6 Means for connecting the container and microscope slide or cover slip mount in a gas-tight manner
7 Seal The ablation chamber 10 according to the invention is suited for direct analysis of small regions of biological samples, for example tissue sections or individual cells, by means of LA-ICP-MS.

Advantageously, instead of a conventional microscope slide frame, the previously mounted laser ablation chamber, together with the microscope slide (which carries the sample and the standard reference materials on the lower face), is introduced from the front into an existing LMD apparatus. The microscope slide, however, can also be fixed on a specially developed stage of the LMD, wherein the mount of the microscope slide can already be part of the stage. The stage here has only a recess of the microscope slide, which is connected in a gas-tight manner from beneath to the container, as a lower part of the laser ablation chamber, by means of a seal (for example by means of screw assemblies or clamp connections). The sample and the standard samples are always located on the lower face of the microscope slide, which is to say at the interior of the laser ablation chamber.

The simplest and most practical variant is to assemble the laser ablation chamber outside of the LMD and introduce it for analysis (microscopy and element analysis) from the front, into the LMD apparatus, so that the analysis region to be examined is moved into the focus of the laser beam. A precise displacement unit already exists in the LMD for inserting the laser ablation chamber. Using this arrangement, in the first step, the sample surface is observed in the fluorescence microscope mode and the analysis region is selected. In the second step, this region is ablated in a defined manner, advantageously using the same arrangement, and mass spectrometrically analyzed with respect to the metal and non-metal distribution. The need for displacement or readjustment of the sample by transferring it into an external laser ablation chamber is thus eliminated.

In a further variant, subsequently, a sample is completely ablated or cut out for further examination. For this purpose, the microscope slide, together with the sample and optional standard samples, is removed from the laser ablation chamber according to the invention and introduced into the conventional original sample stage of the LMD comprising the sample containers beneath, and inserted into the LMD. Specific regions of the sample can now be deliberately cut out in the LMD in the known manner by means of the focused laser beam, and collected in the sample containers located underneath. Using mass spectrometric methods, the structures and sequences of the proteins present in the sample can thus be determined, and additionally the analysis results of the LA-ICP-MS can be validated using ICP-MS after digestion of an analogous sample region. The latter technique can be used to obtain information about the average contents, for example the metal concentrations and phosphorus contents, in the examined sample or standard material.

Thus, in principle, two different procedures are conceivable, which are briefly summarized below:
1. a) The sample is located on a microscope slide in the LDM, optionally together with standard samples. The region to be examined is selected.
   b) The microscope slide remains in the LMD and is assembled with a container (lower part of the laser ablation chamber) to form the laser ablation chamber. The assembly is difficult because of the space constraints beneath the sample stage, but possible in general. The laser ablation chamber is closed in a gas-tight manner. LA-ICP-MS examination of select regions is carried out according to the known analysis protocol.
   c) The microscope slide is removed from the laser ablation chamber and installed individually into the LDM, together with the collection containers for the tissue samples to be cut out.
2. a) The microscope slide, together with the sample and optionally standard samples, is assembled with a container (lower part of the laser ablation chamber) serving to form the laser ablation chamber and inserted into the LMD. First, the regions are selected, and then LA-ICP-MS examination is carried out.
   b) The microscope slide is removed from the laser ablation chamber and installed individually into the LDM, together with the collection containers for the cut-out tissue samples.

In the second proposed and preferred procedure, the laser ablation chamber is assembled with the microscope slide completely outside of the LMD and closed in a gas-tight manner, and is subsequently inserted, for example from the front, into the LMD, and fixed in place. In the variants, the microscope slide also forms the cover slip of the laser ablation chamber. The selected region of the tissue sample to be analyzed is ablated together with the standard samples under the same experimental conditions by means of laser ablation using a laser of the LMD in the proven line scanning mode (line by line). The sample surface is bombarded with photons of a focused laser beam, notably a powerful Nd:YAG laser, wherein the spatial resolution (laser spot diameter) on the surface of the sample should be just a few µm. Suitable devices produce spot diameters of considerably less than 20 µm.

The arrangement of the laser ablation chamber according to the invention, in which the cover is also used as a microscope slide bearing the sample fixed underneath, advantageously allows for a lens of the LMD to extend almost to the microscope slide, and thus almost to the sample. In this way, resolutions as low as the sub-µm range become possible. The ablation of sample material is thus advantageously possible with a spot diameter of less than 1 µm, and more particularly of less than 0.5 µm.

The existing LMD instrumentation can not only be used to microscopically examine the sample surface prior to and after the laser ablation, but in a further step certain regions of the tissue, in which metals and phosphorus were detected, can be deliberately cut out for further analytics of the metalloproteins and collected in sample containers, which are mounted beneath the microscope slide after the laser ablation. For this purpose, the original arrangement of the LMD sample stage comprising the sample containers located beneath must be restored.

FIG. 2 shows the advantageous combination of the laser ablation chamber (10) according to the invention with the existing laser micro dissection device. Instead of the otherwise customary cover slip holder, the entire laser ablation chamber according to the invention, together with the container and microscope slide, can be easily inserted into the LMD device.

As differs from conventional laser ablation chambers, in which the laser beam is generally fixed and only the sample is moved to the desired position by means of an adjusting unit, in a laser dissection device, the sample is generally moved to the correct position for observation by means of the adjustable microscope stage, and subsequently the laser beam is guided by mirrors to the corresponding position. The region to be analyzed is outlined on the monitor using a special pen and is ablated in the line scanning mode after inputting the experimental parameters (laser beam diameter in focus, speed of the laser beam, distance between the lines).

The invention claimed is:

1. A laser ablation chamber, comprising a container having a feed line and a discharge line for a transport gas, a cover slip holder having a cover slip that is transparent to laser light and is also suitable for accommodating a sample, and a means for connecting the cover slip holder and container in a gas-tight manner.

2. The laser ablation chamber according to claim 1, comprising at least one additional seal, which is disposed between the cover slip holder and the container.

3. The laser ablation chamber according to claim 1, comprising clamps or screw assemblies as means for connecting the cover slip holder and container in a gas-tight manner.

4. A laser ablation chamber according to claim 1, comprising a cover slip holder made of Teflon.

5. A laser ablation chamber according to claim 1, comprising a microscope slide as the cover slip.

6. A laser ablation chamber according to claim 1, which is suitable for use in a conventional laser-assisted micro dissection device (LMD).

7. A method according to claim 6, wherein after the laser ablation chamber containing the sample is inserted into the LMD, first a region to be examined is selected and subsequently LA-ICP-MS examination of the selected region is carried out.

8. The method according to claim 7, wherein after the LA-ICP-MS examination, the microscope slide, together with the sample, is removed from the laser ablation chamber and introduced, together with a collection container for cut-out samples, back into the LMD.

* * * * *